(12) United States Patent
Meneghin

(10) Patent No.: US 9,677,208 B2
(45) Date of Patent: Jun. 13, 2017

(54) KNIT WITH BARBS ON BOTH FACES

(75) Inventor: Alfredo Meneghin, Laval (FR)

(73) Assignee: Sofradim Production, Trevoux (FR)

( * ) Notice: Subject to any disclaimer, the term of this patent is extended or adjusted under 35 U.S.C. 154(b) by 479 days.

(21) Appl. No.: 14/239,363

(22) PCT Filed: Aug. 3, 2012

(86) PCT No.: PCT/EP2012/065262
§ 371 (c)(1),
(2), (4) Date: Feb. 18, 2014

(87) PCT Pub. No.: WO2013/026682
PCT Pub. Date: Feb. 28, 2013

(65) Prior Publication Data
US 2015/0299915 A1  Oct. 22, 2015

(30) Foreign Application Priority Data

Aug. 19, 2011  (FR) ...................... 11 02548

(51) Int. Cl.
*D04B 21/12* (2006.01)
*A61F 2/00* (2006.01)

(52) U.S. Cl.
CPC ............ *D04B 21/12* (2013.01); *A61F 2/0063* (2013.01); *A61F 2002/0068* (2013.01); *D10B 2501/0632* (2013.01); *D10B 2509/08* (2013.01)

(58) Field of Classification Search
CPC ..................................................... D04B 21/12
USPC ....................................................... 442/312
See application file for complete search history.

(56) References Cited

U.S. PATENT DOCUMENTS 7,331,199 B2 * 2/2008 Ory ...................... A61F 2/0063
66/170

FOREIGN PATENT DOCUMENTS

| FR | 2949687 A1 | 3/2011 | |
|---|---|---|---|
| GB | 153336 A * | 11/1978 | ............ D04B 21/02 |
| WO | WO 01/81667 A1 | 11/2001 | |
| WO | WO 2010/129641 A1 | 11/2010 | |

OTHER PUBLICATIONS

Specner, David J. Knitting Technology: A Comprehensive Handbook and Practical Guide Third Edition. Woodhead Publishing Limited, Cambridge, England. 2001. pp. 288-294.*
ISO 11676:1994: Textile Machinery and Accessories—Chain Links for Warp Knitting Machines—Vocabulary and Symbols. International Organization for Standardizations, Gevea, Switzerland. Jan. 1, 1994.*
Chinese Office Action corresponding to Chinese Patent Application No. 201280040510.0 dated Sep. 17, 2015.
International Search Report for PCT/EP12/65262 date of completion is Jan. 8, 2013 (2 pages).

* cited by examiner

*Primary Examiner* — Jenna Johnson

(57) ABSTRACT

The present invention relates to a knit with outwardly protruding barbs on each of its faces, said knit being obtained by: i) knitting yarns on at least four guide bars, one bar forming a chain leaving one needle free in two; two bars threaded with monofilament yarn generating loops protruding outwards from the faces of said knit; the fourth bar producing the connection between the yarns of the three other bars, ii) thermosetting the knit obtained at i), iii) forming the barbs by melting the loops. The invention also relates to a prosthesis comprising such a knit.

11 Claims, 2 Drawing Sheets

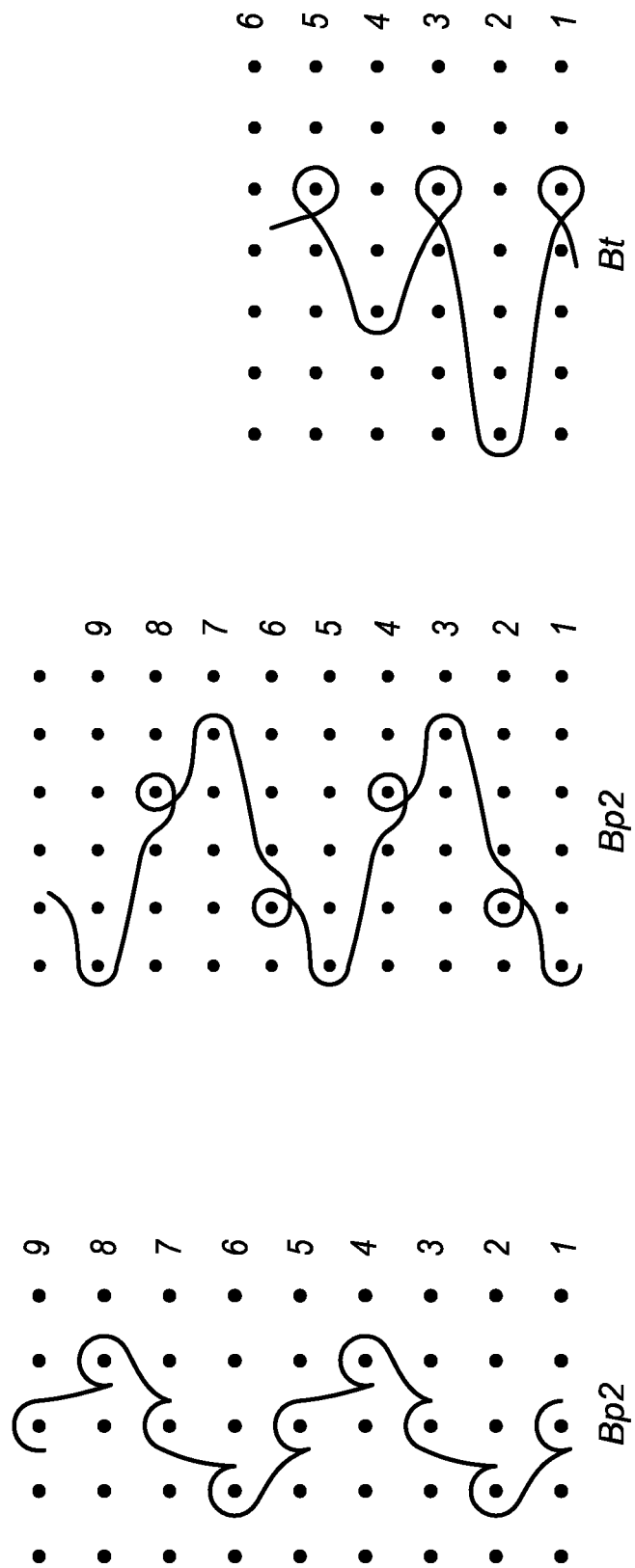

KNIT WITH BARBS ON BOTH FACES

CROSS-REFERENCE TO RELATED APPLICATIONS

This application is a National Stage Application PCT/EP12/65262 under 35 USC §371 (a), which claims priority of French Patent Application Serial No. 11/02548 filed Aug. 19, 2011, the disclosures of each of the above-identified applications are hereby incorporated by reference in their entirety.

The present invention relates to a prosthetic knit with outwardly protruding barbs on each of its faces, said knit being able to be used in particular as a wall reinforcement in parietal and/or visceral surgery.

Wall reinforcement prostheses, for example for the abdominal wall, are widely used in surgery. These prostheses are intended to treat hernias by temporarily or permanently filling a tissue defect. These prostheses are generally made of biocompatible prosthetic fabric and can have a number of shapes, for example rectangular, circular or oval, depending on the anatomical structure to which they are to adapt. Some of theses prostheses are made from entirely bioresorbable yarns and are intended to disappear after they have performed their reinforcing function during the period of cellular colonization and tissue rehabilitation. Others comprise non-bioresorbable yarns and are intended to remain permanently in the body of the patient.

Some of these prostheses are made from an arrangement of yarns, a knit, a woven or non-woven fabric, comprising barbs protruding outwards from one face of the prosthesis: these barbs constitute hooks that are able to fix themselves either in another prosthetic fabric, belonging to the same prosthesis or not, or directly in the biological tissues, for example the abdominal wall.

In some cases, it may be desirable that the textile used for the prosthesis is provided with barbs on each of its faces, so as to be able, for example, to fasten the prosthesis to biological tissues via each of its faces, or to fasten the prosthesis to biological tissues via one of its faces and fasten a second prosthetic textile to the opposite face, by means of these barbs.

The document WO01/81667 describes the production of a textile comprising barbs on only one of its faces.

The production of a textile comprising barbs protruding outwards from each of its faces can comprise the manual step in which a textile, as described in WO01/81667, is provided with barbs or hooks on the face remaining without barbs after the knitting. However, such work is time-consuming and awkward.

The applicant has found a quick and simple method of producing a knit with outwardly protruding barbs on its two opposite faces.

The present invention relates to a prosthetic knit comprising an arrangement of yarns defining at least two faces for said knit, said knit being provided, on each of its faces, with barbs protruding outwards from said face, said knit being obtained by the following steps:
 i) knitting, on a warp knitting machine, yarns distributed on at least four guide bars, comprising needles m, said four bars operating according to a defined chart repeat; one of the four bars, the bar Bc, forming a chain stitch and being threaded 1 full, 1 empty, so as to leave free the needles (m+i), where i is an odd number and not zero; two other bars, the bars Bp1 and Bp2, each threaded with monofilament yarn, each placing said monofilament yarn as an overlap on one and the same free needle (m+i) once every four rows of said chart repeat, said overlaps of the bar Bp1 being offset by two rows in relation to those of the bar Bp2 for one and the same free needle (m+i), said overlaps generating loops protruding outwards from the faces of said knit, namely from a first face for the bar Bp1 and from the opposite face for the bar Bp2; the fourth bar, the bar Bt, operating according to said chart repeat so as to generate weft yarns producing the connection between the yarns of the three other bars,
 ii) thermosetting the knit obtained at i),
 iii) forming barbs by melting the loops.

Another aspect of the present invention is a process for manufacturing a prosthetic knit comprising an arrangement of yarns defining at least two faces for said knit, said knit being provided, on each of its faces, with barbs protruding outwards from said face, said process comprising the following steps:
 i) knitting, on a warp knitting machine, yarns distributed on at least four guide bars, comprising needles m, said four bars operating according to a defined chart repeat; one of the four bars, the bar Bc, forming a chain stitch and being threaded 1 full, 1 empty, so as to leave free the needles (m+i), where i is an odd number and not zero; two other bars, the bars Bp1 and Bp2, each threaded with monofilament yarn, each placing said monofilament yarn as an overlap on one and the same free needle (m+i) once every four rows of said chart repeat, said overlaps of the bar Bp1 being offset by two rows in relation to those of the bar Bp2 for one and the same free needle (m+i), said overlaps generating loops protruding outwards from the faces of said knit, namely from a first face for the bar Bp1 and from the opposite face for the bar Bp2; the fourth bar, the bar Bt, operating according to said chart repeat so as to generate weft yarns producing the connection between the yarns of the three other bars,
 ii) thermosetting the knit obtained at i),
 iii) forming the barbs by melting the loops.

The knit according to the invention has barbs on both faces, and the manufacture of the knit according to the invention can be performed in a single knitting step, without requiring any supplementary step. Thus, the knit according to the invention can be manufactured simply and quickly and does not require a manual step of fastening barbs to one of the faces after the knitting. The knit according to the invention can thus be produced industrially. Such a knit can thus be fastened to biological tissues via each of its faces. Alternatively, such a knit can be fastened to biological tissues via one of its faces, a second prosthetic textile being able to be fastened to the opposite face of said knit, by means of these barbs. In another alternative, the knit according to the invention can be fastened, by way of its barbs, to two other textiles, one on each of its faces: it can thus be useful for joining two textiles without the need to use staples.

Furthermore, melting the monofilament loops makes it possible to obtain barbs having a head with dimensions greater than the diameter of the monofilament, said head thus being well suited to its functions of fastening and fixing, either to biological tissues or to other textiles, in particular openwork textiles. Within the meaning of the present invention, openwork textile means the characteristic whereby a textile has pores, or voids, cells, holes or orifices that are open and distributed uniformly or non-uniformly and that promote cellular colonization. The pores can be present in all sorts of forms, for example spheres, channels and hexagonal shapes.

Each loop of the knit according to the invention is cut in two on account of its melting and thus gives rise to two barbs protruding outwards from the face on which the loop is present.

The yarns used to manufacture the knit according to the invention are yarns of biocompatible material which may or may not be bioresorbable. In one embodiment, the monofilament yarns threaded on the bars Bp1 and Bp2 are chosen from among yarns of polypropylene, polyglycolic acid, polylactic acid and mixtures thereof. For example, the monofilament yarns threaded on the bars Bp1 and Bp2 are of polylactic acid. In one embodiment, the diameter of said monofilament yarns varies from 0.12 to 0.18 mm. Such a diameter makes it possible to obtain barbs having a good ability to fasten in the biological tissues or in another openwork textile.

In one embodiment, the yarns threaded on the bars Bc and Bt are chosen from among monofilament and/or multifilament yarns. The multifilament yarn count can range from 50 dtex to 100 dtex. The diameter of the monofilament yarns can range, for example, from 0.08 to 0.10 mm. Any yarn made of biocompatible and optionally bioresorbable material can be used. For example, the yarns threaded on the bars Bc and Bt can be of polyester, polypropylene, polylactic acid, polyglycolic acid and mixtures thereof.

In one embodiment, the bar Bc is threaded 1 full, 1 empty according to the following chart according to the standard ISO 11676:

Bc: 1.0/0.1//

Such a stitch is known to a person skilled in the art in the field of textiles and is a chain stitch: such a stitch is able to give the knit a resistance in the chain direction. Moreover, the 1 full, 1 empty threading of the bar forming the chain makes it possible to leave one needle in two free, said free needle thus being able to generate a loop when one of the bars Bp1 or Bp2 places its yarn as an overlap on this needle. Conversely, the needle not left free generates a collar that imprisons the monofilament yarn, thereby securing the foot of the barb obtained after the loop has melted. With such a stitch, it is thus possible to prevent the barbs from separating from the knit or from being torn from the knit during use.

In some embodiments, the bar Bp1 is threaded 1 full, 3 empty according to the following chart according to the standard ISO 11676:

Bp1: 0.0/2.1/5.5/3.4// and the bar Bp2 is threaded 1 full, 3 empty according to one of the following charts according to the standard ISO 11676:

Bp2: 5.5/3.4/0.0/2.1//
or
Bp2: 1.2/2.3/2.1/1.0//
or
Bp2: 1.2/3.2/2.1/0.1//
and the bar Bt is threaded 1 full, 1 empty according to one of the following charts according to the standard ISO 11676:

Bt: 1.0/5.5/1.0/3.3//
or
Bt: 0.0/3.3/0.0/5.5//

The bars Bp1 and Bp2 are those threaded with the monofilament yarns that are first going to give loops by knitting and that will then subsequently give rise to the barbs after the step of melting the loops. Thus, the above charts make it possible to form loops on both faces of the knit and adapt the surface density of the barbs to the desired type of fastening.

The bar Bt makes it possible to produce a backing weft that gives the knit its coherence and its stability.

In one embodiment, step iii) is performed by placing each face of said knit on a cylinder that is brought to a temperature that causes the loops to melt and thus form the barbs.

Another aspect of the invention is a prosthesis comprising at least one knit as described above. Such a prosthesis can be advantageously used as a wall reinforcement in parietal or visceral surgery, in particular for the treatment of hernias.

The invention will be better understood from the following detailed description and examples, and also from the figures, in which:

FIG. 3 is a schematic view showing the stitch provided by the bar Bp2 in another embodiment of the knit according to the invention.

FIG. 4 is a schematic view showing the stitch provided by the bar Bp2 in another embodiment of the knit according to the invention.

FIG. 5 is a schematic view showing the stitch provided by the bar Bt in another embodiment of the knit according to the invention.

Figure 1:
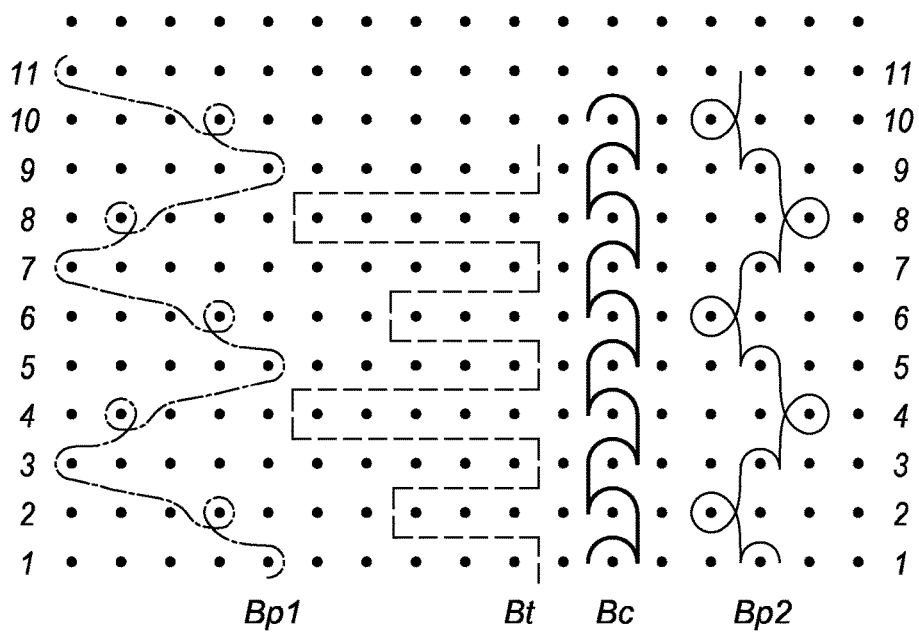
FIGS. 1 and 2 are schematic views of the charts of four bars of a warp knitting machine, respectively showing them individually and together, permitting production of a knit according to the invention.

A prosthetic knit according to the invention is produced on a warp knitting machine with 4 guide bars Bc, Bp1, Bp2 and Bt, as have been described above, where the bar Bp2 is in position 1 on the knitting machine, the bar Bc is in position 2, the bar Bt is in position 3, and the bar Bp1 is in position 4. The threadings and the stitches are the following, according to the standard ISO 11676:

To make the first face of the knit:

Bc: 1.0/0.1//

The bar Bc forming the chain and being threaded 1 full, 1 empty, and

Bp2: 1.2/2.3/2.1/1.0//

The bar Bp2 being threaded 1 full, 3 empty and being intended to produce the barbs of the first face.

To Make the Opposite Face:

Bt: 0.0/3.3/0.0/5.5//

The bar Bt being threaded 1 full, 1 empty and being intended to form the weft yarns connecting the yarns of the three other bars, and Bp1: 0.0/2.1/5.5/3.4//

The bar Bp1 being threaded 1 full, 3 empty and being intended to produce the yarns of the opposite face.

This stitch is illustrated in FIG. 1, which indicates the bars Bc, Bp1, Bp2 and Bt and, for each bar, the path of a yarn (indicated by a fine line for Bc, by a dot-and-dash line for Bp1, by a solid line for Bp2 and by dashes for Bt). In this figure, the numbers 1 to 11 indicate the stitch rows of the knit.

Figure 2:
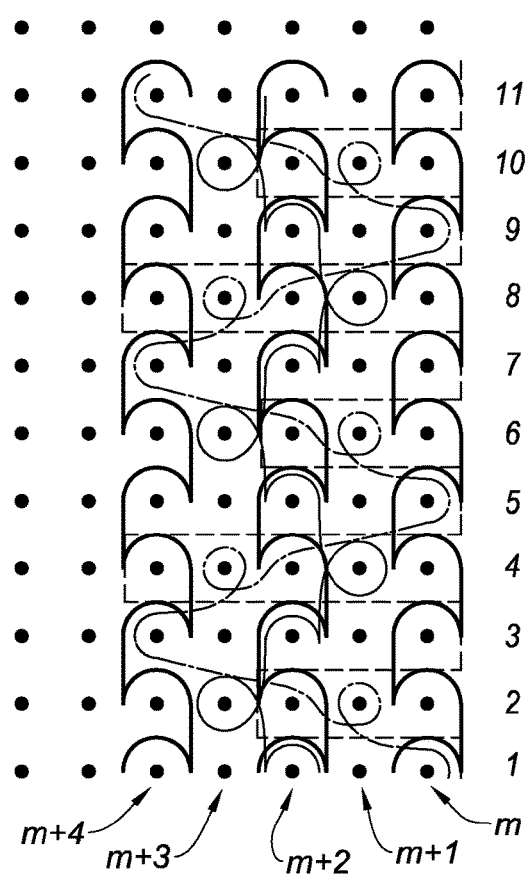

FIG. 2 also indicates the needles m, (m+1), (m+2), (m+3) and (m+4), the paths of the yarns of the 4 bars being shown together on a set of 5 needles.

The yarns threaded on the bars Bp1 and Bp2 are monofilaments of polylactic acid (PLA). The yarns threaded on the bar Bc forming a chain are monofilaments of polyester. The yarns threaded on the bar Bt forming the weft are also monofilaments of polyester.

Alternatively, if the aim was to manufacture a totally bioresorbable knit, the yarns threaded on the bars Bc and Bt could be monofilaments of PLA.

As will be seen clearly from FIG. 2, the bar Bc forming a chain is threaded 1 full, 1 empty and thus leaves free one needle in two, namely the needles (m+i), where i is an odd number and not zero, the needles (m+1) and (m+3) in FIG. 2.

As will also be seen from FIGS. 1 and 2, the bar Bp1 places its overlap yarn on one and the same free needle once every 4 rows of the chart repeat: thus, referring to FIG. 2, the bar Bp1 places its overlap yarn on the needle (m+1) at row 2, then again at row 6, then at row 10. This same bar Bp1 places its overlap yarn on the needle (m+3) at row 4, then at row 8, and so on (not shown in the figure).

Likewise, the bar Bp2 places its overlap yarn on one and the same free needle once every 4 rows of the chart repeat: thus, referring to FIG. 2, the bar Bp2 places its overlap yarn on the needle (m+1) at row 4, then at row 8. This same bar Bp2 places its overlap yarn on the needle (m+3) at row 2, then at row 6, then at row 10, and so on (not shown in the figure).

This type of stitch, as described in this example, makes it possible to directly produce, by knitting, a knit which, on each of its two faces, has loops capable of giving rise to outwardly protruding barbs.

Each time an overlap yarn is placed on a needle by one of the bars Bp1 and Bp2, a loop protruding to the outside of the knit is formed. In the present case, the bar Bp1 forms loops protruding outwards from one face of the knit, while the bar Bp2 forms loops protruding outwards from the other face of the knit.

Moreover, as can be seen from FIG. 2, the overlap yarns of the bar Bp1 are offset by two rows in relation to those of the bar Bp2 for one and the same free needle (m+i), for example for the free needle (m+1), or for the free needle (m+3).

This type of weave, as described in this example, makes it possible to directly produce, by knitting, a knit which, on each of its two faces, has loops capable of giving rise to outwardly protruding barbs.

Thus, once the knit has been produced as indicated above, it is thermoset, for example at 110° C., in order to stabilize it in length and width.

Once the knit has been thermoset, each face of the knit is placed in contact with a cylinder containing an electrical heating resistor so as to melt the loops present on said face. On melting, each loop cuts in two and gives rise to two barbs protruding outwards from the face of the knit, each barb preferably having a head with dimensions greater than those of the diameter of the monofilament yarn forming the initial loop.

Such a knit can be used as it is, directly as a prosthesis in parietal or visceral surgery for wall reinforcement. Alternatively, this knit can be combined with another textile, with two textiles (one on each face), or with an anti-adhesion film on one or both of its faces. The barbs can be covered with an anti-adhesion coating to prevent them from becoming entangled in the body of the knit when the latter is folded up on itself, for example in order to be introduced into a trocar.

EXAMPLE 2

A knit identical to that of Example 1 is produced, except that the chart of the bar Bp2 is the following according to the standard ISO 11676:

Bp2: 1.2/3.2/2.1/0.1//

FIG. 3 illustrates this chart.

Such a knit also has outwardly protruding loops on both of its faces. After thermosetting and formation of the barbs as described in Example 1, this knit can be used as a prosthesis or for the manufacture of prostheses in parietal or visceral surgery.

EXAMPLE 3

A knit identical to that of Example 1 is produced, except that the chart of the bar Bp2 is identical to that of the bar Bp1, but offset by two rows. This chart is therefore the following, according to the standard ISO 11676:

Bp2: 5.5/3.4/0.0/2.1//

FIG. 4 illustrates this chart.

Such a knit also has outwardly protruding loops on both of its faces. In particular, the chart of the bar Bp2 being identical to that of the bar Bp1, the knit has two identical faces, hence an identical surface density of the barbs on both faces. After thermosetting and formation of the barbs as described in Example 1, this knit can be used as a prosthesis or for the manufacture of prostheses in parietal or visceral surgery.

EXAMPLE 4

A knit identical to that of Example 3 is produced, except that the chart of the bar Bt is the following according to the standard ISO 11676:

Bt: 1.0/5.5/1.0/3.3//

FIG. 5 illustrates this chart.

Such a knit also has outwardly protruding loops on both of its faces. After thermosetting and formation of the barbs as described in Example 1, this knit can be used as a prosthesis or for the manufacture of prostheses in parietal or visceral surgery.

The invention claimed is:

1. A prosthetic knit comprising an arrangement of yarns defining at least two faces for said knit, said knit being provided, on each of its faces, with barbs protruding outwards from said face, said knit being obtained by the following steps:
   i) knitting, on a warp knitting machine, yarns distributed on at least four guide bars, comprising needles m, said at least four guide bars operating according to a defined chart repeat; first guide bar Bc, forming a chain stitch and being threaded 1 full, 1 empty, so as to leave free needles (m+i), where i is an odd number and not zero; second and third guide bars Bp1 and Bp2, each threaded with monofilament yarn, each placing said monofilament yarn as an overlap on one and the same free needle (m+i) once every four rows of said chart repeat, said overlaps of the second guide bar Bp1 being offset by two rows in relation to those of the third guide bar Bp2 for one and the same free needle (m+i), said overlaps generating loops protruding outwards from a first face of said knit for the second guide bar Bp1 and from a second face of said knit opposite the first face for the third guide bar Bp2; fourth guide bar Bt, operating according to said chart repeat so as to generate weft yarns producing a connection between the yarns of the first, second, and third guide bars,
   ii) thermosetting the knit obtained at i),
   iii) forming the barbs by melting the loops.

2. The prosthetic knit according to claim 1, wherein the monofilament yarns threaded on the second and third guide bars Bp1 and Bp2 are chosen from among yarns of polypropylene, polyglycolic acid, polylactic acid and mixtures thereof.

3. The prosthetic knit according to claim 1, wherein said monofilament yarns threaded on the second and third guide bars Bp1 and Bp2 have a diameter from 0.12 to 0.18 mm.

4. The prosthetic knit according to claim 1, wherein the yarns threaded on the first and fourth guide bars Bc and Bt are chosen from among monofilament and/or multifilament yarns.

5. The prosthetic knit according to claim 1, wherein step iii) is performed by placing each face of said knit on a cylinder that is brought to a temperature that causes the loops to melt and thus form the barbs.

6. A process for manufacturing a prosthetic knit comprising an arrangement of yarns defining at least two faces for said knit, said knit being provided, on each of its faces, with barbs protruding outwards from said face, said process comprising the following steps: i) knitting, on a warp knitting machine, yarns distributed on at least four guide bars, comprising needles m, said four bars operating according to a defined chart repeat; first guide bar Bc, forming a chain stitch and being threaded 1 full, 1 empty, so as to leave free needles (m+i), where i is an odd number and not zero; second and third guide bars Bp1 and Bp2, each threaded with monofilament yarn, each placing said monofilament yarn as an overlap on one and the same free needle (m+i) once every four rows of said chart repeat, said overlaps of the second guide bar Bp1 being offset by two rows in relation to those of the third guide bar Bp2 for one and the same free needle (m+i), said overlaps generating loops protruding outwards from a first face for the second guide bar Bp1 and from a second face of said knit opposite the first face for the third guide bar Bp2; fourth guide bar Bt, operating according to said chart repeat so as to generate weft yarns producing a connection between the yarns of the first, second, and third guide bars,
    ii) thermosetting the knit obtained at i),
    iii) forming the barbs by melting the loops.

7. The process according to claim 6, wherein the monofilament yarns threaded on the second and third guide bars Bp1 and Bp2 are chosen from among yarns of polypropylene, polyglycolic acid, polylactic acid and mixtures thereof.

8. The process according to claim 7, wherein said monofilament yarns threaded on the second and third guide bars Bp1 and Bp2 have a diameter from 0.12 to 0.18 mm.

9. The process according to claim 6, wherein the yarns threaded on the first and fourth guide bars Bc and Bt are chosen from among monofilament and/or multifilament yarns.

10. The process according to claim 6, wherein step iii) is performed by placing each face of said knit on a cylinder that is brought to a temperature that causes the loops to melt and thus form the barbs.

11. The process comprising at least one knit according to claim 1 or obtained by the process according to claim 6.

* * * * *